(12) United States Patent
Michelson

(10) Patent No.: US 8,121,665 B2
(45) Date of Patent: Feb. 21, 2012

(54) METHOD AND DEVICE FOR THE EXAMINATION OF CAVITIES

(75) Inventor: Georg Michelson, Baiersdorf (DE)

(73) Assignee: Heidelberg Engineering Optische Messsysteme GmbH, Dossenheim (DE)

( * ) Notice: Subject to any disclaimer, the term of this patent is extended or adjusted under 35 U.S.C. 154(b) by 1782 days.

(21) Appl. No.: 10/509,443

(22) PCT Filed: Mar. 28, 2003

(86) PCT No.: PCT/EP03/03264
§ 371 (c)(1),
(2), (4) Date: Jun. 28, 2005

(87) PCT Pub. No.: WO03/082085
PCT Pub. Date: Oct. 9, 2003

(65) Prior Publication Data
US 2005/0261595 A1    Nov. 24, 2005

(30) Foreign Application Priority Data

Mar. 28, 2002  (DE) .................................. 102 14 360

(51) Int. Cl.
*A61B 5/05* (2006.01)

(52) U.S. Cl. ........ 600/407; 600/437; 600/452; 600/476; 351/205

(58) Field of Classification Search .......... 600/407–480; 351/205, 206
See application file for complete search history.

(56) References Cited

U.S. PATENT DOCUMENTS

| 5,309,916 A | * | 5/1994 | Hatschek | 600/485 |
| 5,900,928 A | | 5/1999 | Riva et al. | |
| 6,078,397 A | * | 6/2000 | Monchalin et al. | 356/503 |
| 7,055,955 B2 | * | 6/2006 | Kishida et al. | 351/205 |
| 2002/0131017 A1 | * | 9/2002 | Kishida et al. | 351/206 |

FOREIGN PATENT DOCUMENTS

EP    0 631 757    1/1995

OTHER PUBLICATIONS

Fischer et al., "Analysis of pressurized resistance vessel diameter changes with a low cost digital image processing device", 1996, Computer Methods and Programs in Biomedicine, vol. 50, No. 1, pp. 23-30.*

Joerg-Gerald Fischer et al., "Analysis of pressurized resistance vessel diameter changes with a low cost digital image processing device"; Computer Methods and Programs in Biomedicine, vol. 50, No. 1, Jun. 1996, pp. 23-30.

E. Nagel et al.; "Messug retinaler Gefaessdurchmesser mittels Scanning-Laser-Opthalmoskop und Computer"; Opthalmologe, vol. 89, No. 5, Oct. 1992, pp. 432-436.

\* cited by examiner

*Primary Examiner* — Brian Casler
*Assistant Examiner* — Nasir Shahrestani
(74) *Attorney, Agent, or Firm* — Jordan and Hamburg LLP

(57) ABSTRACT

The invention relates to a method and furthermore a device from the examination of cavities, in particular an eye, by means of laser scanning. The aim of the invention is to carry out further investigations, above all with respect to possible diseases. Said aim is achieved, whereby the determination of the cavity wall thickness, in particular of retinal cavities is carried out. The external diameter and the internal diameter are determined by scanning doppler laser and the wall thickness determined from the data recorded thus.

17 Claims, 1 Drawing Sheet

METHOD AND DEVICE FOR THE EXAMINATION OF CAVITIES

The invention relates to a method for examining blood vessels, in particular of the eye and more particularly of the retina. The invention furthermore relates to an apparatus for performing the method.

Known from EP 0 631 757 B1 are such a method and such an apparatus, which are embodied for measuring the flow velocity of a liquid, in particular blood. The frequency shift of a laser beam reflected in the liquid is determined in accordance with the optical Doppler effect, whereby two-dimensional grid-field scanning is performed by means of the laser beam. The Doppler shift is calculated from the temporal variation in the measured intensity of the reflected light and the flow velocity is determined therefrom.

Retinal vessels are the mirror of the vascular system. Arteriosclerotic vessel changes in the brain are associated with changes in ocular fundus vessels. Generalized and focal constrictions in retinal vessels, signs of arteriovenous crossing, and retinal microinfarcts have a strong correlation to hypertension and stroke. In one epidemiological study (Beaver Dam Eye Study), it could be demonstrated that the prevalence of retinal emboli was 0.3% between the ages of 43 and 54, 1.2% between the ages of 55 and 64, 1.3% between the ages of 65 and 74, and 3.1% is people older than 75 years of age. After adjusting the control group for age, sex, and systemic factors, people with retinal emboli have a 2.6-times greater risk of dying as a result of stroke. The authors concluded that discovery of retinal emboli in a non-symptomatic patient with introduction of early therapy in terms of the underlying basic illness is advantageous for the patient's prognosis.

In one study with 11,000 subjects, the ocular fundus was examined with respect to retinal vascular abnormalities and a possible connection to arterial blood pressure. The authors were able to demonstrate by means of conventional ophthalmological examination methods that for every 10-mmHg increase in mean arterial pressure, first, the ratio of arterial and venous diameter decreased by 0.2 units, and, second, focal arterial constrictions increased with an odds ratio of 2. Furthermore, a linear correlation between blood pressure and the retinal vessel risk index was identified. The image data processed were evaluated by purely manual measurements.

Stroke, one of the most severe consequences of arterial hypertension, is avoidable. International studies clearly demonstrate that up to a 70% reduction in stroke can be achieved by purposefully and resolutely reducing risk factors for stroke, especially high blood pressure. Of decisive importance for successfully preventing terminal organ damage due to arterial hypertension within the overall population is identifying and treating endangered patients with high vascular risk. Investigating a retinal vessel risk index that indicates vascular damage to the cerebrovascular system could be employed for targeted screening for a risk of stroke in large segments of the population. In many vascular illnesses, the cause of the lack of oxygen is thickening of the vascular wall. It is known that the thickness of the internal carotid artery intima-media represents a very important risk factor when evaluating the risk of arteriosclerosis.

Starting from this point, the object of the invention is to further develop the method and the apparatus of the aforesaid type such that further examinations of retinal vessels can be performed with low complexity. The examinations should yield precise measurement results that in particular provide important information about any diseases the person being examined has and/or about the health of the person being examined. In addition, novel fields of application and employment shall open up for the method and the apparatus, which is also called an ophthalmoscope.

With respect to the method, this object is achieved by laser Doppler scanning a blood vessel thereby to determine exterior diameter thereof and interior diameter thereof and, from the foregoing, wall thickness of the blood vessel, i.e., vascular wall thickness. With regard to the apparatus, the object is achieved by the apparatus's comprising a laser Doppler scanner for producing a first image or a first set of data corresponding to exterior diameter of the vessel and a second image or a second set of data corresponding to interior diameter of the vessel and an evaluation unit for determining vascular wall thickness of the vessel from the first and second images or sets of data.

The inventively suggested method and the apparatus suggested for the performance thereof enable the vascular wall thickness of retinal vessels to be determined without particular complexity. This creates substantially broadened employment options for scanning laser devices and/or ophthalmoscopes. In particular, the examinations cited in the foregoing can be performed with great precision so that necessary therapies can be introduced based on risks established in this manner. The inventive non-invasive determination of the vascular wall thickness of retinal vessels enables screening of broad segments of the population with minimum complexity, whereby early detection of any disease can substantially improve the quality of life of the patient in question and in addition substantial reductions in costs can be obtained in terms of health care.

The scanning laser Doppler flowmetry measurement method enables simultaneous representation of retinal vessels by means of reflectivity and by means of the laser Doppler shift. The reflectivity images yield the external diameter of the retinal vessels, the Doppler images yield the diameter of the blood column moved. The vascular wall thickness of retinal vessels is determined from the difference of the two images. The vascular wall thickness can be determined by comparing the moved blood column (laser Doppler image) to the entire vessel (reflectivity images). Since the retina represents a visible portion of the brain, vascular risk in terms of oxygen supply to the brain can be assessed by observing retinal vessels. One very important parameter is vascular wall thickness. In accordance with the invention, non-invasive determination of vascular wall thickness of retinal vessels occurs by means of scanning laser Doppler.

Further developments and special embodiments of the invention are provided in the subordinate claims and in the following specification.

The invention is explained in greater detail using the drawings without this imposing any restriction.

FIG. 2 is the reflectivity image upon which FIG. 1 is based;

FIG. 4 is the laser Doppler image upon which FIG. 3 is based.

Figure 1:
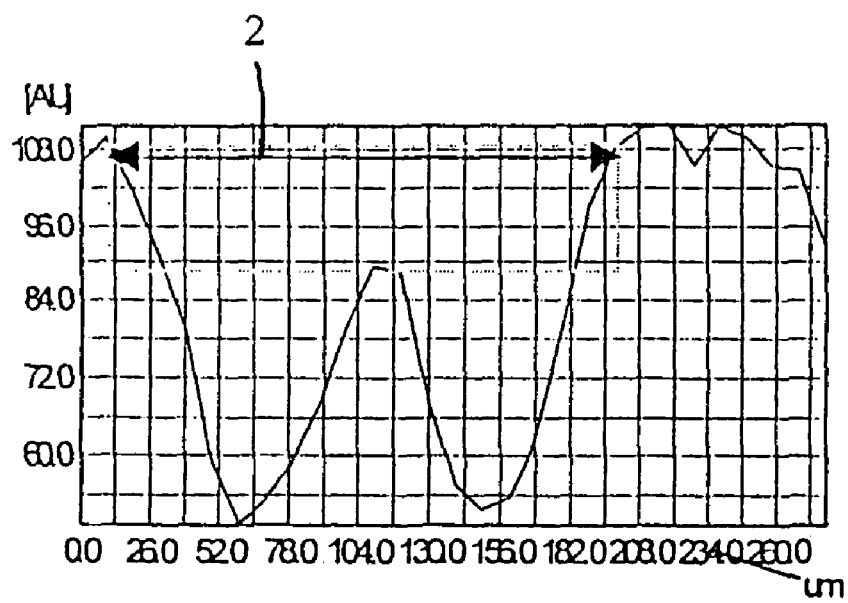
FIG. 1 is a diagram with data for a retinal vessel that have been determined from a reflectivity image.
Figure 2:

FIG. 1 is a typical diagram, corresponding to a retinal vessel, the reflectivity image of which is shown in FIG. 2. The exterior diameter of the vessel is marked with the arrow 2. At least an approximation of the distance between the two maximum values is acquired between which are the minimum values corresponding to the vessel walls. The abscissa is divided into micrometers and thus the external diameter of the vessel is 190 µm.

Figure 3:
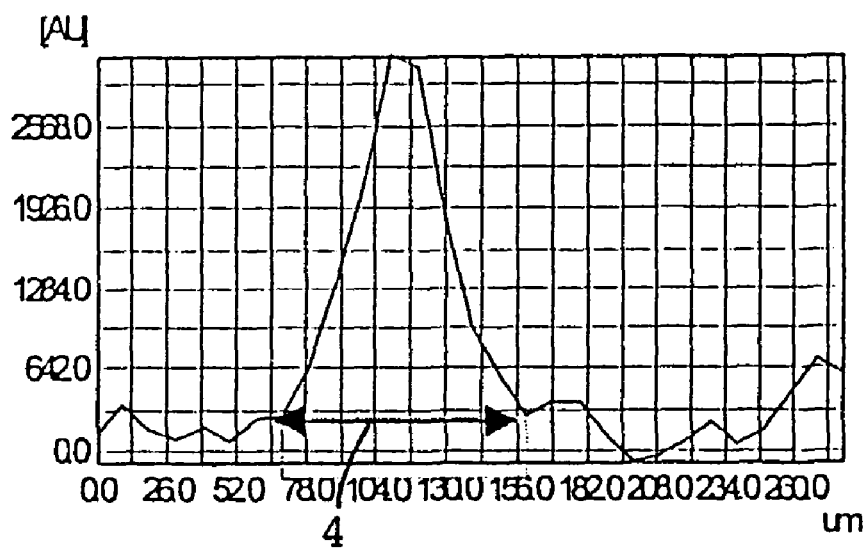
FIG. 3 is a diagram of the data for a retinal vessel that have been determined from a laser Doppler image.
Figure 4:
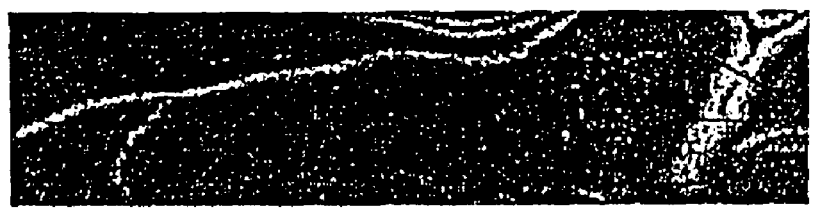

The diagram in FIG. 2 illustrates a typical course corresponding to a moved blood column after evaluation of the laser Doppler image shown in FIG. 3. Such a laser Doppler image can be produced for instance by the method for measuring flow velocity of the blood or the device embodied appropriately, described in the cited EP 0 631 757. The inventor recognized that the interior diameter of the vessel can be deduced by imaging and determining the moved blood column. Until today from a practical aspect and in particular given achievable measurement precision it has not been possible to measure the vessel interior directly. On the contrary, in accordance with the invention the interior diameter is measured indirectly by determining the moved blood column. Taking into account the abscissa scale of diagram 2, given in μm, in accordance with arrow 4 the vessel has an interior diameter of 90 μm.

The vessel wall thickness is determined from values obtained in this manner for the exterior diameter and the interior diameter of the vessel in a preferred manner and with little complexity, in particular in terms of computer performance, by finding the difference or correlating these data.

In the apparatus for performing the method, the evaluation unit provided in a laser device for examining the ocular fundus or image evaluation is employed, whereby in addition the computer of the apparatus is embodied such that finding the difference or correlating the data determined is performed inventively.

The invention claimed is:

1. A method for examining a blood vessel, comprising:
   laser Doppler scanning a blood vessel, thereby to determine an exterior diameter thereof and an interior diameter thereof; and
   determining vascular wall thickness of the blood vessel based upon determination of said exterior diameter and said interior diameter in said laser Doppler scanning, said determination of the exterior diameter being from data collected in a reflectivity image resulting from the laser Doppler scanning.

2. A method according to claim 1, wherein the determination of the interior diameter is from data determining a diameter of a moving blood column in the vessel.

3. A method according to claim 2, wherein the data determining the diameter of a moving blood column is data collected in a laser Doppler image resulting from the laser Doppler scanning.

4. A method according to claim 3, wherein the vascular wall thickness is determined by determining a difference between data collected in the reflectivity image and data collected in the laser Doppler image.

5. A method according to claim 1, wherein the vessel is of an eye.

6. A method according to claim 5, wherein the vessel is of a retina.

7. An apparatus for examining a blood vessel to determine vascular wall thickness thereof, comprising:
   a laser Doppler scanner for producing a first image or a first set of data corresponding to the first image relating to exterior diameter of the vessel and a second image or a second set of data corresponding to the second image relating to interior diameter of the vessel, said first image being a reflectivity image resulting from a laser Doppler scanning by said laser Doppler scanner; and
   an evaluation unit configured for determining vascular wall thickness of the vessel from the first and second images or sets of data.

8. An apparatus according to claim 7, wherein the laser Doppler scanner is for producing the second image or the second set of data by determining diameter of a moving blood column in the vessel.

9. An apparatus according to claim 7 or 8, further comprising a computer for said determining the vascular wall thickness from said first and second images or sets of data.

10. An apparatus according to claim 7 or 8, wherein the laser Doppler scanner is for producing the images or the data corresponding thereto of a blood vessel of an eye.

11. An apparatus according to claim 7 or 8, wherein the laser Doppler scanner is for producing the images or the data corresponding thereto of a blood vessel of a retina.

12. A method for examining a blood vessel, comprising:
   scanning the blood vessel with a Doppler laser;
   acquiring reflectivity image data of the blood vessel resulting from the scanning with the Doppler laser;
   acquiring Doppler image data of a moving blood column in the blood vessel;
   determining an exterior diameter of the blood vessel from the reflectivity image data;
   determining an interior diameter of the blood vessel from the Doppler image data of the moving blood column; and
   determining a vascular wall thickness of the blood vessel by determining a difference of the exterior diameter and the interior diameter of the blood vessel.

13. A method according to claim 12, wherein the blood vessel is in an eye.

14. A method according to claim 13, wherein the blood vessel is of a retina.

15. An apparatus for examining a blood vessel by performing the method of claim 12, comprising:
   a Doppler laser for scanning the blood vessel; and
   a computer configured to acquire the reflectivity image data of the exterior diameter of the blood vessel and Doppler image data of a moving blood column in the blood vessel, to determine an exterior diameter of the blood vessel from the reflectivity image data, to determine an interior diameter of the blood vessel from the Doppler image data of the moving blood column and to determine a vascular wall thickness of the blood vessel by determining a difference of the exterior diameter and the interior diameter of the blood vessel.

16. An apparatus according to claim 15, wherein the Doppler laser is for scanning the blood vessel in an eye.

17. An apparatus according to claim 16, wherein the Doppler laser is for scanning the blood vessel of a retina.

* * * * *